(12) United States Patent
Vicenzi et al.

(10) Patent No.: US 11,801,076 B2
(45) Date of Patent: Oct. 31, 2023

(54) ARTHRODESIS DEVICE

(71) Applicant: Orthofix S.R.L., Bussolengo (IT)

(72) Inventors: Federico Vicenzi, Verona (IT); Andrea Zaccaria, Tregnago (IT); Daniele Venturini, Povegliano Veronese (IT); Denis Lorenzini, Caprino Veronese (IT)

(73) Assignee: Orthofix S.R.L., Verona (IT)

( * ) Notice: Subject to any disclaimer, the term of this patent is extended or adjusted under 35 U.S.C. 154(b) by 0 days.

(21) Appl. No.: 17/801,179

(22) PCT Filed: Mar. 18, 2021

(86) PCT No.: PCT/EP2021/056956
§ 371 (c)(1),
(2) Date: Aug. 19, 2022

(87) PCT Pub. No.: WO2021/185971
PCT Pub. Date: Sep. 23, 2021

(65) Prior Publication Data
US 2023/0098345 A1 Mar. 30, 2023

(30) Foreign Application Priority Data

Mar. 18, 2020 (IT) .................. 102020000005719

(51) Int. Cl.
*A61B 17/72* (2006.01)
*A61B 17/74* (2006.01)

(52) U.S. Cl.
CPC ...... *A61B 17/7225* (2013.01); *A61B 17/7241* (2013.01); *A61B 17/744* (2013.01)

(58) Field of Classification Search
CPC ...... A61B 17/72; A61B 17/7216–7225; A61B 17/7233–7241
See application file for complete search history.

(56) References Cited

U.S. PATENT DOCUMENTS

| 9,308,031 B2 | 4/2016 | Elghazaly et al. |
| 2005/0187550 A1* | 8/2005 | Grusin ............... A61B 17/7241 606/62 |

(Continued)

OTHER PUBLICATIONS

European Patent Office, International Search Report and Written Opinion for PCT/EP2020/056958, dated Jun. 4, 2021, 10 pages.

(Continued)

*Primary Examiner* — Eduardo C Robert
*Assistant Examiner* — Michelle C Eckman
(74) *Attorney, Agent, or Firm* — HAYNES AND BOONE, LLP

(57) ABSTRACT

The present invention relates to an improved orthopaedic device for athrodesis, in particular for the arthrodesis or fusion of a joint, for example an ankle joint, of the type comprising of a nail having head and tip ends opposed to each other; at least a first portion of the nail having an axis of symmetry; a single circular first transverse hole made in the first portion near the head of the nail and extended according to its own axis perpendicularly to the axis of symmetry; a slotted second transverse hole still made in the first portion of the nail and extended perpendicular to both the first axis of symmetry; and to the axis of the first transverse hole; and the slotted second transverse hole being made at a greater distance with respect to the head of the nail than the distance from the head of the first transverse hole.

20 Claims, 19 Drawing Sheets

(56) References Cited

U.S. PATENT DOCUMENTS

| | | | |
|---|---|---|---|
| 2008/0221577 A1* | 9/2008 | Elghazaly | A61B 17/7241 606/62 |
| 2012/0130370 A1* | 5/2012 | Kinmon | A61B 17/7241 606/62 |
| 2017/0296241 A1* | 10/2017 | Garlock | A61B 17/7291 |
| 2018/0177537 A1* | 6/2018 | Van Dyke | A61B 17/8665 |
| 2019/0274742 A1 | 9/2019 | Garlock et al. | |

OTHER PUBLICATIONS

European Patent Office, International Preliminary Report on Patentability for PCT/EP2020/056956, dated Feb. 9, 2022, 14 pages.

* cited by examiner

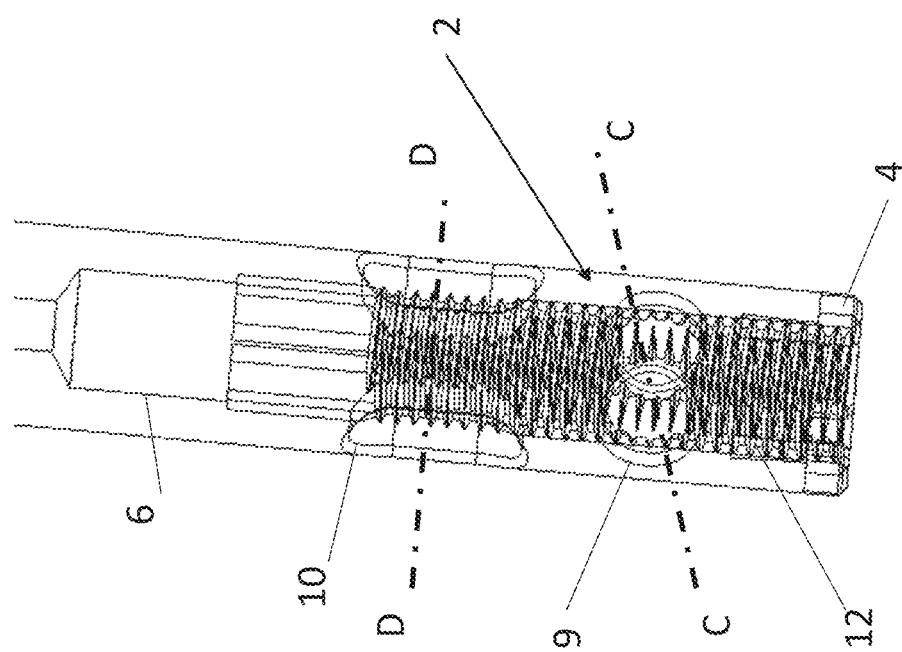

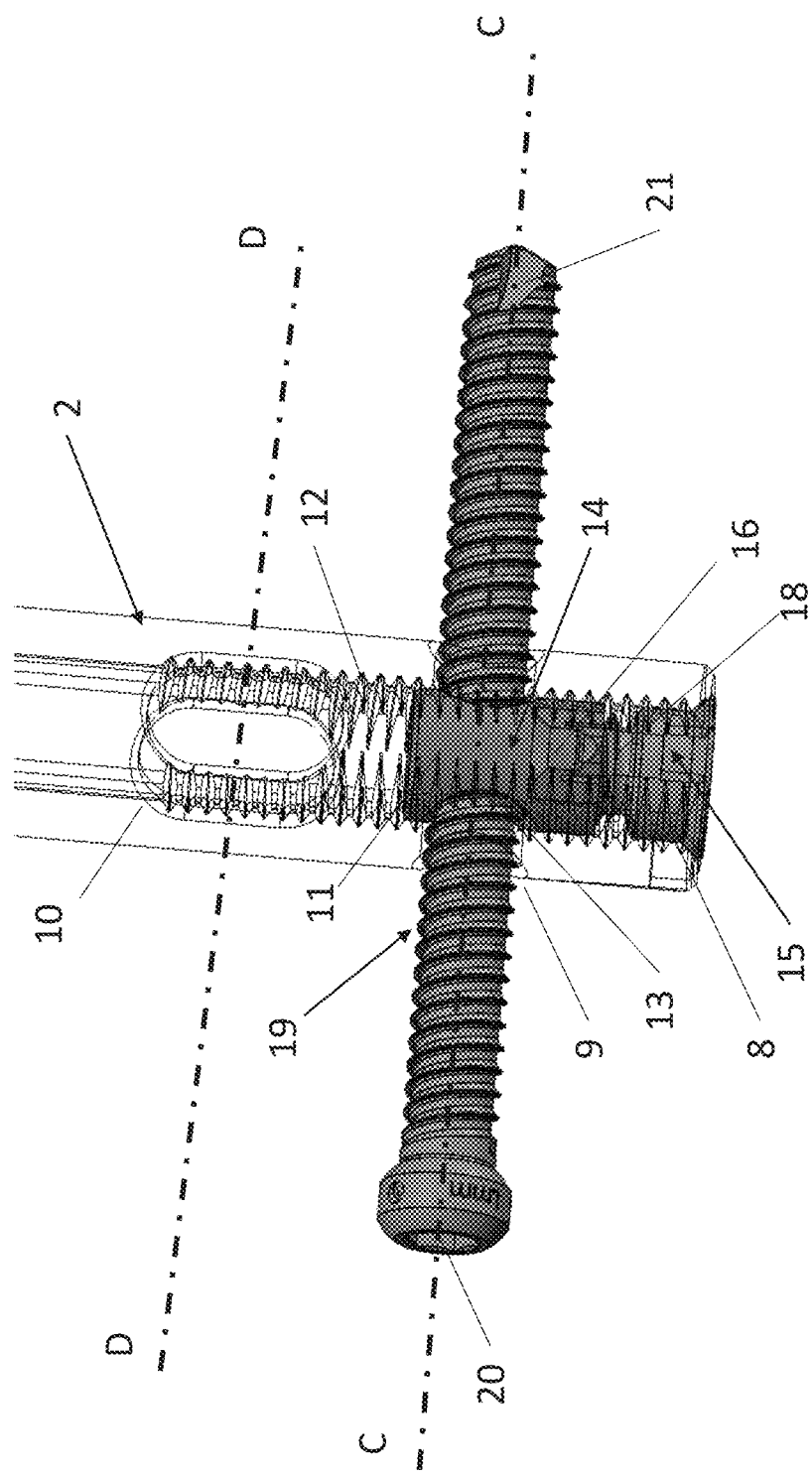

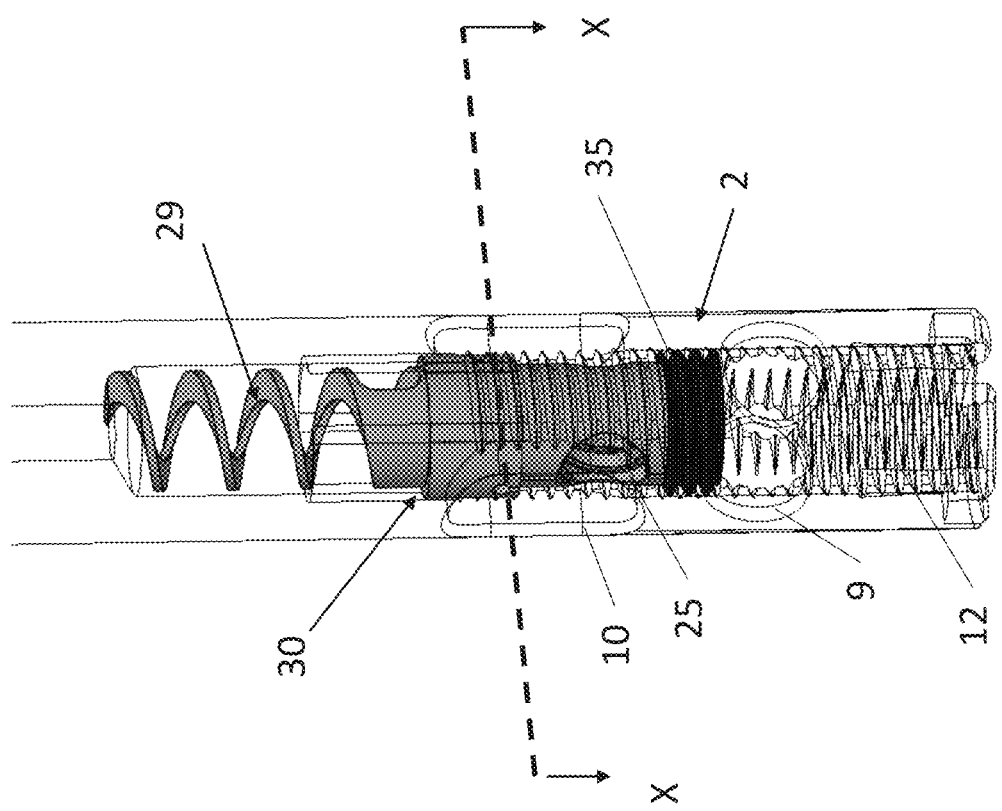

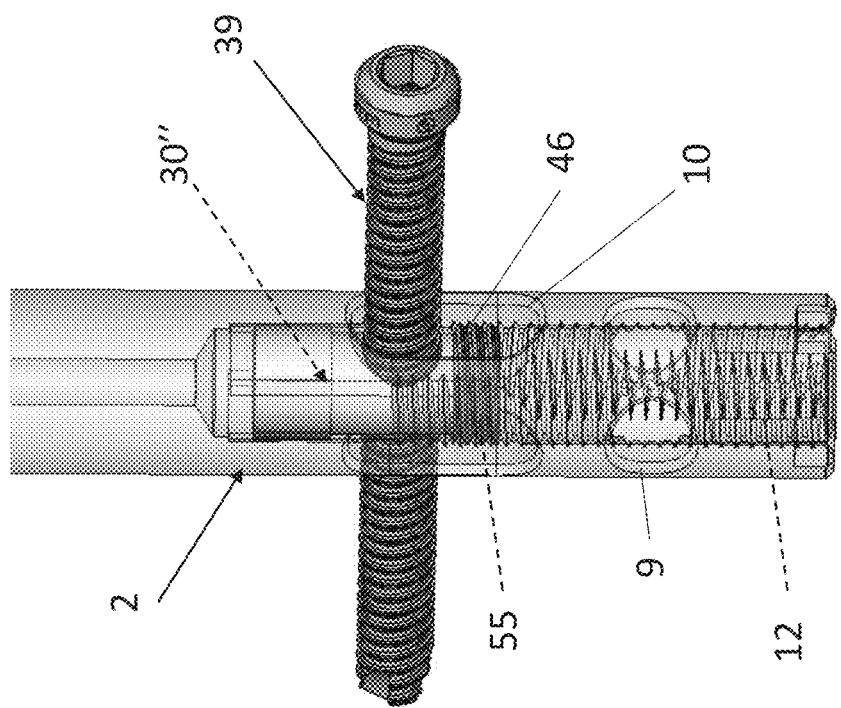
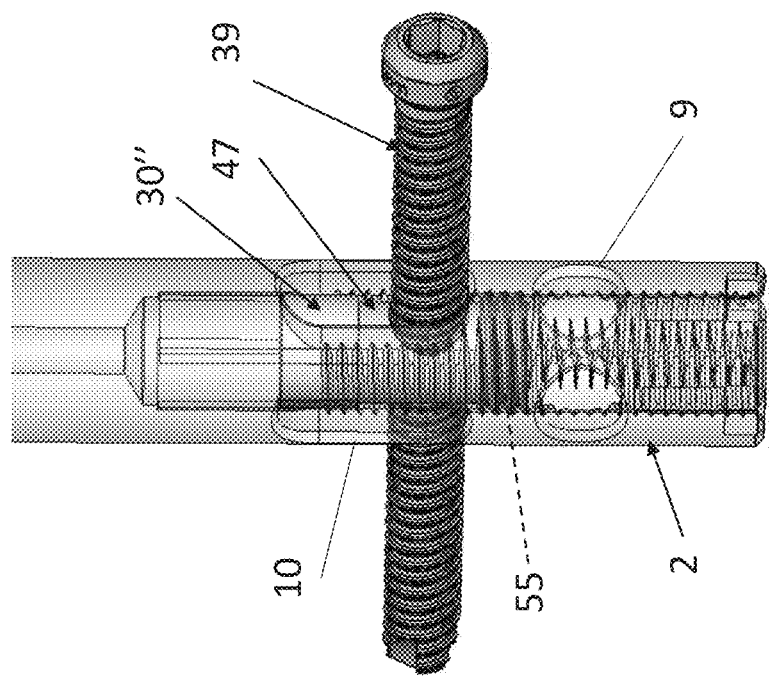
FIG. 16B
FIG. 16A

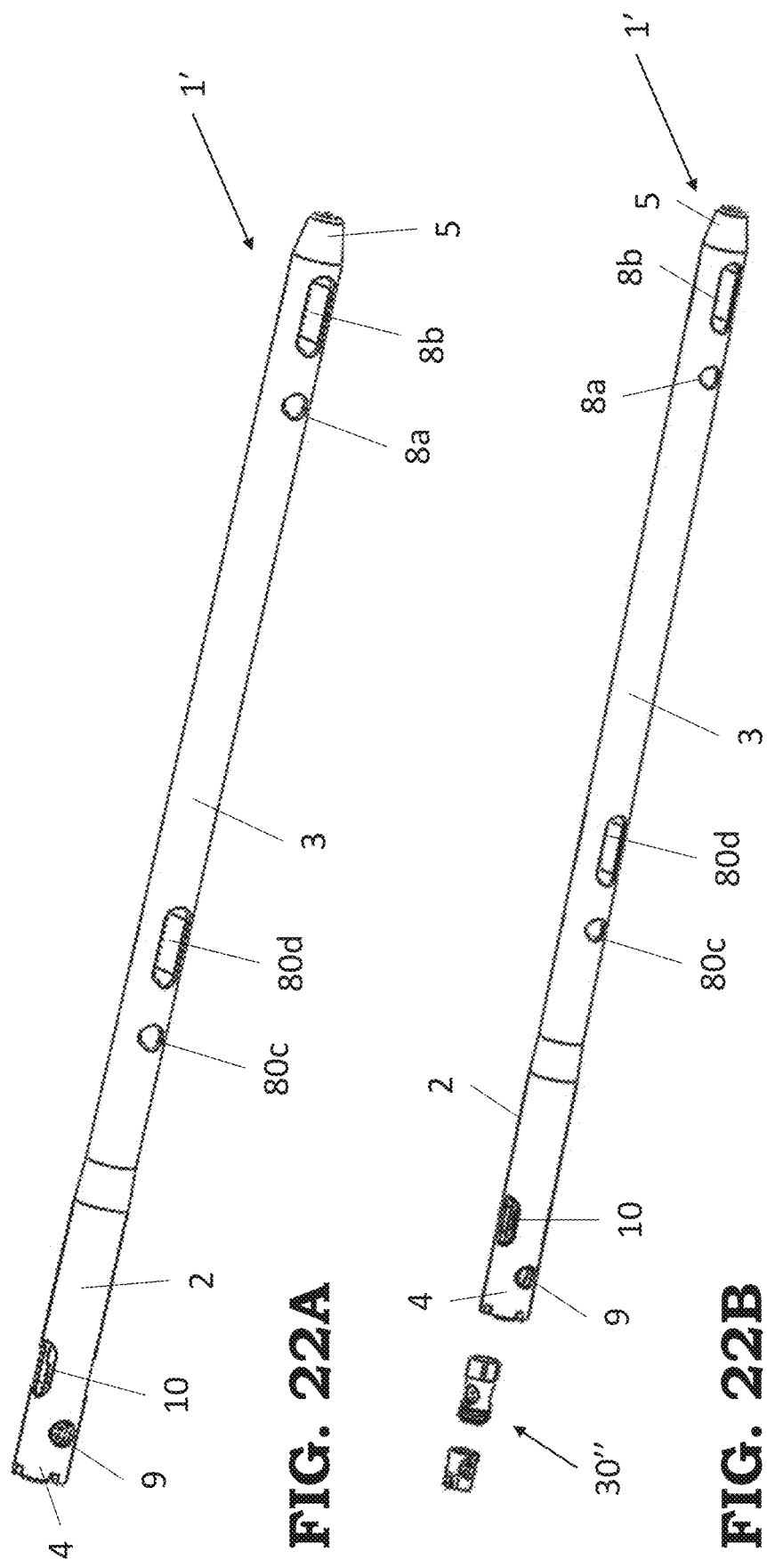

ARTHRODESIS DEVICE

This application is a national phase application of PCT/EP2021/056956, filed Mar. 18, 2021, which claims priority to and the benefit of Italy Application No. 102020000005719, filed Mar. 18, 2020, both of which are incorporated herein in their entireties.

FIELD OF APPLICATION

The present invention relates to the general technical field of devices provided to be used for carrying out an arthrodesis or fusion and, more specifically, for carrying out an arthrodesis of the ankle joint, in particular in the context of orthopaedic treatment.

More in particular, the invention relates to an orthopaedic device provided for a subastralgic joint and at the tibiotarsic joint in order to obtain a stable fastening of the ankle.

The invention more precisely relates to an improved device for arthrodesis, in particular for the arthrodesis or fusion of a joint, for example an ankle joint, of the type comprising:
  a nail having head and tip ends opposed to each other; and
  at least a first portion of the nail having an axis of symmetry.

PRIOR ART

In order to treat some bone pathologies of the ankle, such as severe arthrosis, which causes decay or disappearance of the articular cartilage, it is known to proceed with the arthrodesis of the joint of the affected ankle.

This is a surgical operation provided to suppress all or part of the mobility of the ankle joint, causing osteosynthesis (or "bone fusion") of the present bone bodies.

In order to perform these operations, it is known to use a device for arthrodesis comprising a nail for arthrodesis, provided to be implanted at the level of the ankle joint. In short, an arthrodesis (fusion) between calcaneus and talus (subastralgic joint) and between talus and tibia (tibiotarsic joint) is created in order to form a solid and movement-free construction which does not cause continuous pain to the patient, so that he can still carry out the normal daily activities.

The nail is generally introduced into housings, which are successively formed, through the various bone bodies which form the affected joint, fastening it in seat so as to immobilize the ankle joint and promote the bone fusion of these bone bodies.

A known nail of this type is described for example in the patent document EP 1 848 355 B1 and provides three through holes made in the distal part for corresponding fastening screws placed at different angles in order to increase the stabilization of the joint.

A second known technical solution is instead described in EP 2 254 492 B1 in which an intramedullary device for the TTC arthrodesis procedure is disclosed and comprises substantially parallel holes at the tibia and calcaneus of the patient.

A further known solution is described in application n. WO 2019/155160 A1 which describes a device for arthrodesis comprising a screw in the calcaneus, a screw in the talus and a connecting screw between talus and calcaneus.

Nails according to the prior art are also disclosed, for instance, in US 2018/177537 A1, US 2002/072748 A1 and U.S. Pat. No. 9,308,031 B2.

Substantially, the known solutions provide nails comprising:
  two holes to place the screws in the calcaneus (the most distal in the posteroanterior calcaneus, the most proximal in the mediolateral calcaneus);
  a hole (or a slot) to place the screw in the (mediolateral) talus.

In addition, almost all nails on the market comprise an internal mechanism at the level of the talus which allows the talus itself to be compressed against the tibia in order to allow fusion between the two bones to take place. Normally, this is a screw positioned inside the slot and which can be pushed upwards by a threaded dowel inside the nail. There is also a solution which uses a NiTiNOL alloy rod which causes a continuous compression based on the super-elasticity of this alloy.

All these arthrodesis devices are generally satisfactory and have so far led to a marked improvement in the treatment of patients affected by advanced bone pathologies of the ankle.

However, there are also pathologies which cannot be efficiently treated with the nails of the known solution.

For example, in the case of a diabetic foot which extends up to the ankle, it is possible to ascertain an absence or the absence of mechanical resistance of the talus which is in general due to a structural collapsing thereof.

In this case it is not possible to insert an ankle-related screw since it is structurally insufficient or the bone for which it is provided is at all absent. In these cases, the hole or the ankle-related slot is left without a screw, but this hole is often located around the transition area between tibia and calcaneus, which is particularly stressed.

Since the hole is located in a much-stressed area of the nail which becomes a critical area which is often subject to breakages of the device.

There are also situations which require an inspection of the implantation of the nail, for example in the event of failure of the treatment with a standard nail due to an infection or other problems. In these cases, it is possible that a prosthesis or ankle fusion plates are not desired or cannot be used, but that the use of another nail is desired, in which case one is forced to implant the new screws by placing them in the holes where the previous screws were located.

Due to the small sizes of the bones in the foot, the new nail cannot be moved too much with respect to the previous one since there would be an excessive protrusion of the nail from the calcaneus or the implantation of a screw in a joint. All this makes the new fastening precarious since the screws are inserted in previously used holes in the bone and it has been noted that in some cases there may be a lack of stability during use with a risk of imperfect osteosynthesis of the bone bodies of the ankle.

The technical problem underlying the present invention is to provide a new improved orthopaedic device, in particular for the arthrodesis of an ankle joint, having structural and functional features such as to remedy the above-mentioned drawbacks and to guarantee an excellent stability once implanted in the ankle joint of a patient, while allowing a better maintenance of the bone bodies of the ankle in order to facilitate the bone fusion of the latter.

Another object of the invention is to provide a new device for arthrodesis comprising a nail which can be stabilized in a particularly efficient way during implantation in the bone bodies of the ankle joint.

Another object of the invention is to provide a new device for arthrodesis comprising a nail for arthrodesis with a design which is simple and inexpensive to manufacture.

Another object of the invention is to provide a new device for arthrodesis which allows an efficient compression of the ankle joint.

SUMMARY OF THE INVENTION

The solution idea underlying the present invention is to provide a device for arthrodesis comprising a nail provided with a single distal mediolateral hole, at the calcaneus, and a rear-front proximal slot, also at the calcaneus.

Based on the above-mentioned solution idea, the technical problem is solved by an improved orthopaedic device for arthrodesis, in particular for the arthrodesis or fusion of a joint, for example an ankle joint, of the type comprising:
- a nail having distal head and proximal tip ends opposed to each other;
- at least a distal first portion of the nail having an axis of symmetry;
- at least a proximal second portion of the nail;
- a single circular first transverse hole made in the first portion near the head of the nail and extended according to its own axis perpendicularly to said axis of symmetry, said single circular first transverse hole being arranged to accommodate a bone screw oriented along a mediolateral direction in a patient's calcaneus:
- a slotted second transverse hole still made in the first portion of the nail and extended perpendicular to both said first axis of symmetry, and to the axis of the first transverse hole, said slotted second transverse hole being arranged to accommodate a fastening screw oriented along a posteroanterior direction in the patient's calcaneus;
- the slotted second transverse hole being made at a greater distance with respect to the head of the nail than the distance from the head of said first transverse hole.

It is observed that, as it is always the case for TTC arthrodesis devices of the present type, the second portion has at least a proximal hole, preferably a plurality of proximal holes, made in the second portion near the tip and arranged to accommodate bone screws oriented along a mediolateral direction of the patient's tibia.

Advantageously, said first portion of the nail has an internal cavity extended starting from the head along said axis of symmetry and internally comprising a thread extended up to at least said slotted second transverse hole. Such thread is extended up to at least 80% of the slotted second hole.

Furthermore, fastening means—in particular a bone screw—are inserted in said circular first transverse hole and pass through a locking element inserted inside the first portion of the nail.

A closing plug for the head of the nail is furthermore provided, said closing plug being structured with a first stage fastened to the free end of the head and an internal second stage in engagement with a sleeve locking element inserted in the first portion of the nail and provided with a transverse hole accessible through said circular first transverse hole.

The locking element is made of a bio-compatible material or a synthetic-plastic material with predetermined elasticity features, as well as partially yielding material. In a preferred embodiment, this locking element is made of a titanium alloy. This sleeve locking element is internally threaded up to said transverse hole in order to be engaged by an external thread of said second stage.

It should also be noted that the sleeve locking element comprises two appendices opposed to each other provided for a screwing engagement in a thread provided in an internal cavity of said first portion of the nail and extended starting from the head along said axis of symmetry up to passing said circular first transverse hole.

A compression mechanism is also provided with elastic element inserted in said first portion of the nail between a support dowel screwed into said thread of the internal cavity and a constriction of said first portion; a transverse hole being provided in a base portion of said mechanism in order to be accessible through said slotted second transverse hole.

The elastic element is a helical spring integral with said base portion or associated in a structurally independent manner to said base portion.

Other types of compression mechanisms are also provided, as described in the following description and in the dependent claims. Said compression mechanisms all comprise a transverse hole, the position of which may be regulated. A fastening screw is inserted transversely through the slotted second transverse hole of the distal first portion and said transverse hole of the compression mechanism.

The features and advantages of the invention will be and become more evident from the description provided below of an example of embodiment given with reference to the attached drawings, provided solely by way of illustrative and non-limiting example, in which:

BRIEF DESCRIPTION OF THE DRAWINGS

FIG. 3 shows a schematic and prospective view of the distal portion of the device of FIG. 2;

FIG. 4 shows a schematic and perspective view of the distal portion of the device of FIG. 2 equipped with fastening means;

FIG. 8 shows a prospective and schematic view of the compression mechanism of FIG. 7A inserted inside the device for arthrodesis according to the invention;

FIGS. 16A and 16B show respective prospective and schematic views of the improved device for arthrodesis according to the present invention equipped with the component parts illustrated in FIGS. 14 to 15B;

FIG. 22A shows a prospective view of a second embodiment of a nail according to the invention;

FIG. 22B shows a prospective view of the nail of FIG. 22A with the compression mechanism of FIG. 18 extracted for illustration purpose.

DETAILED DESCRIPTION

The invention relates to an improved device for arthrodesis and provided to be used for the arthrodesis of the ankle joint of a patient, in particular when the latter is in an advanced state of decay due to a series of pathologies such as for example a serious arthrosis.

The ankle arthrodesis device according to the invention is, more specifically, a Tibia-Talus-Calcaneus (TTC) arthrodesis device of the retrograded type. For example, the device for arthrodesis according to the invention can be advantageously used to treat a patient affected by an advanced form of degenerative arthrosis, port-traumatic arthrosis, inflammatory arthritis, talus necrosis, Charcot osteoarthropathy or even in case of failure of one or more surgical operations, such as an arthroplasty operation or in the previously remarked situation of substantial absence of talus.

Figure 1:
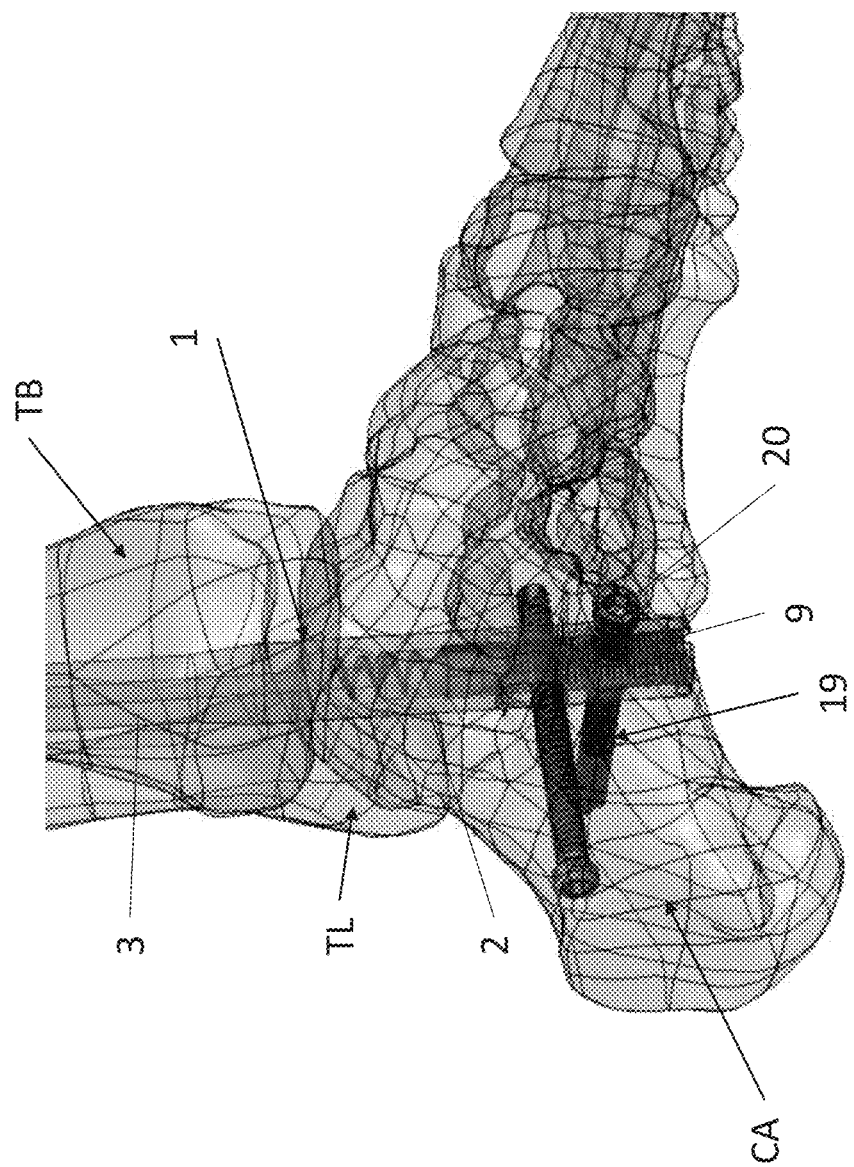
FIG. 1 illustrates a partial and prospective schematic view of an improved device for arthrodesis according to the present invention and shown as implanted in a human foot.

As shown in FIG. 1, the device for arthrodesis according to the invention comprises a nail for arthrodesis 1 provided to be implanted, preferably in a plantar way, in a tibia TB, a talus TL and a calcaneus CA of a patient, generally during a surgical operation.

Normally, the implantation of the device 1 is preceded by a suitable preparation stage so as to completely or partly suppress the natural articular surfaces of the ankle joint to be treated, in order to facilitate the bone fusion. Furthermore, a suitable accommodation seat of the nail 1 is provided in the tibia TB, in the talus TL and in the calcaneus CA and is obtained according to conventional methods to make orthopaedic holes.

In the rest of the present description, reference will be made to a sagittal plane of the patient and the part or portion closest to the sole of the foot and the insertion side of the nail 1 will be defined as distal and the part or portion furthest away from the sole of the foot will be defined as proximal.

In a preferred embodiment, the nail 1 has an enlarged distal portion 2 and a proximal portion or shaft 3 with smaller diameter.

The enlarged distal portion 2 is the portion closest to the head 4 of the nail 1 and is the one which crosses calcaneus CA, talus TL and the part of the tibia TB associated with the talus TL.

The nail 1 also has a side tip end 5 (shown in FIGS. 22A, 22B) opposed with respect to the head 4 and rounded in a conventional way.

The innovations of the nail 1 of the present invention mainly relates to the distal portion 2 or head portion of the nail and, for this reason, the most part of the figures only relates to this portion of the nail 1.

The nail 1 is monolithic and thus formed in a single piece. The piece can be moulded, extruded and/or turned. Furthermore, the nail 1 is made of inherently bio-compatible material or material which was made bio-compatible after a treatment and able to withstand to the characteristic biomechanical stresses of the implantation area, i. e. an ankle, and for the time necessary to allow the bone fusion. The materials can be stainless steel, titanium alloy, chrome-cobalt alloy, or a polymeric material, such as for example loaded or not loaded polyether-ether-ketone (PEEK).

Figure 2:
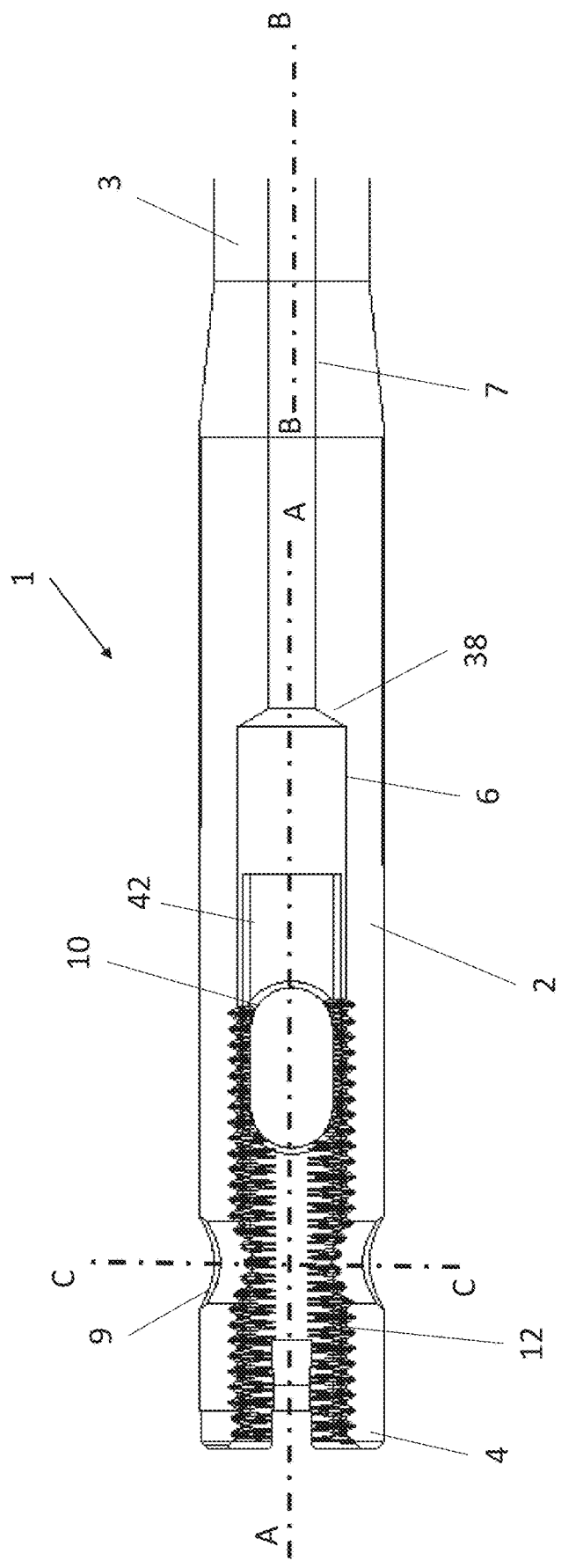
FIG. 2 shows a lateral schematic view of a distal portion of the device according to the present description.

As shown in FIG. 2, the distal part 2 of the nail 1 has an own axis of symmetry A-A, while the distal part 3 has its own axis of symmetry B-B. The two axes can coincide or be sloped of some degrees with respect to each other without limiting in any way the rights of the applicant.

According to the embodiment illustrated in the figures, the proximal part 2 and the distal part 3 are both elongated and substantially respectively straight according to said directions of the respective axes A-A and B-B of extension.

Preferably, both the distal part 2 and the proximal part 3 are cannulated and have respective extended internal cavities 6 and 7 for all the length of the corresponding portions 2 and 3.

The cavity 6 of the distal portion 2 is with circular section and a greater diameter with respect to the cavity 7 of the portion 3. The two cavities 6 and 7 are communicating and jointed with each other in a segment 38, practically a constriction, being still internally part of the distal portion 2.

Both the distal portion 2, and the proximal portion 3, of the nail 1 have a generally cylindrical shape with a circular section. Alternatively, both the portions could have a slightly conical shape always with a circular shape. Also a sectional oval shape is equally feasible as well as a combination of all these possible shapes.

Advantageously, the distal portion 2 of the nail 1 has an extended transverse hole 9 according to an own axis C-C perpendicular to the axis A-A of longitudinal extension of the distal portion 2.

With respect to the known solutions, this first transverse hole 9 is the only one circular hole provided in the distal portion 2 of the nail 1 at the calcaneus CA.

Due to the cylindrical shape of the distal portion 2, the end openings of the transverse hole 9 opposed to each other are concave as shown in FIG. 2.

The transverse hole 9 is provided to accommodate a fastening means 19 in order to block the nail 1 rotating around the axis of extension A-A. Such fastening means 19 is a bone screw with Allen head 20 visible in FIG. 1.

The screw fastening means 19 are inserted in said circular first transverse hole 9 and are passing through a locking element 14 inserted inside the first portion 2 of the nail 1 and described below.

Advantageously, it is provided a non-circular second through hole 10 in turn extended perpendicularly to the axis A-A of longitudinal extension of the distal portion 2.

Aside from the first and second transverse holes 9 and 10, the distal portion 2 is not traversed by any further hole for accommodating bone screws.

The second transverse hole 10 has its own axis of symmetry D-D, visible in particular in FIG. 3; such axis is perpendicular to the axis C-C of the first transverse hole 9.

The second transverse hole 10 is slotted and is obtained in a more proximal position with respect to the first transverse hole 9, i. e. in a position further away with respect to the head 4 of the nail 1, but always at the calcaneus CA when the device 1 is implanted in the patient.

The first transverse hole 9 can be defined as distal mediolateral while the second transverse hole 10 is a proximal slot perpendicular to the first transverse hole 9.

Furthermore, always according to the present description, the internal cavity 6 of the distal portion 2 of the nail 1 is internally threaded starting from the head 4.

The thread 12 of the internal cavity 6 is extended from the head end 4 of the nail 1 up to the most part of the slotted second hole 10; up to at least around 80 or 90% of the extension of the slot.

In FIG. 4, a further prospective and schematic view of the distal portion 2 of the nail 1 is shown in which a fastening screw 19 is inserted which crosses the first transverse hole 9.

The screw 19 is internally threaded and has an Allen head 20.

The external thread of the screw 19 is engaged by the openings of the transverse hole 9 opposed to each other. In this way, the screw 19 is firmly transversally held in the distal portion 2 of the nail 1 and can be further screwed in the calcaneus CA via the self-threading tip 21.

Advantageously, it is also provided a locking element 14 to firmly block the screw 19 inside the first transverse hole 9 such that it cannot slide when the device is implanted in the joint of the patient.

The locking element 14 is made of a bio-compatible and implantable material and comprises a sleeve 11 crossed by a transverse hole 13. The locking element 14 has an own elastic deformation capability inherent to the used material.

Two guiding and stabilizing appendices 16, 17 opposed to each other are also provided, of which only the first is visible in FIG. 4, in order to fit the locking element 14 inside the cavity 6 by friction and/or by pushing up to the point where the transverse hole 13 matches with the first transverse hole 9 of the distal portion 2 of the nail 1 in a substantially coaxial way. The section of the cavity 6 (visible in a following FIG. 9) is not perfectly circular, but has lateral concavities 40 and 42 opposed to each other and more or less evident, in order to facilitate the holding in a correct position of the locking element 14 which, in an operating condition, is accommodated with the appendices 16 and 17 and held in the lateral concavities 40 opposed to each other.

A closing plug 15 of the head 4 of the nail 1 is further provided. The plug 15 has a structure with two stages with a first stage 8 with countersunk end inserted in a flushed and vanishing way in the mouth of the internal thread 12 of the cavity 6 at the head 4 of the nail and a second coaxial stage 18 but with smaller diameter and which is externally threaded in order to be screwed in the locking element 14, as will be seen here below.

Figure 5:
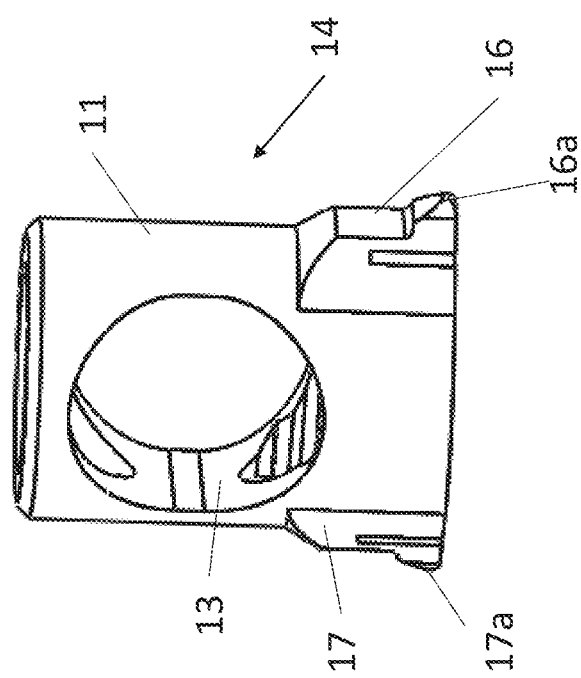
FIG. 5 shows a prospective and schematic view of a locking element incorporated in the device according to the present description.

FIG. 5 shows a prospective and schematic view of the locking element 14 inserted inside the cavity 6 such that the transverse hole 13 matches with the circular first transverse hole 9 of the nail 1.

The locking element 14 is structured with a sleeve 11 from which the two appendices 16 and 17 opposed to each other are projecting.

Each of such appendices ends with a tab-like tip 16a, 17a in order to increase the friction and facilitate the holding in seat of the locking element 14 inside the cavity 6 with the appendices 16 and 17 accommodated and held in the lateral concavities 40.

The sleeve 11 has an internal thread 22 provided to be engaged by the second stage 18 of the closing plug 15 of the head 4 of the nail 1.

Figure 6:
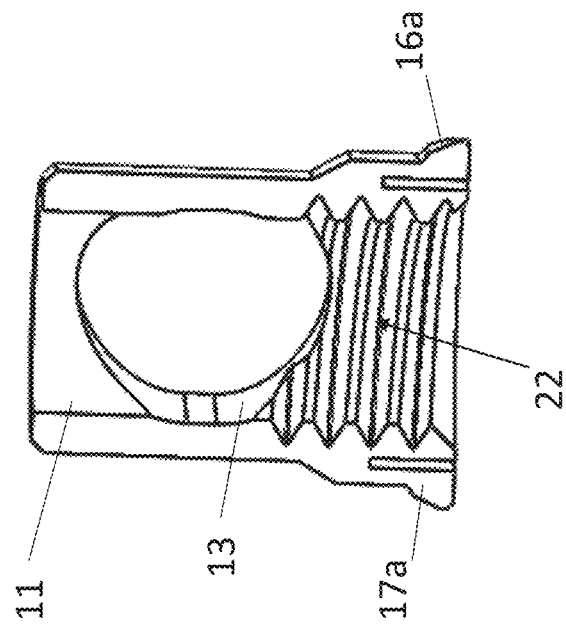
FIG. 6 shows a further prospective and schematic, but sectional, view of the locking element of FIG. 5.

In FIG. 6, the internal structure of the sleeve 11 of the locking element 14 is shown more in detail.

The thread 22 is extended up to the transverse hole 13.

When the second stage 18 of the plug 15 is screwed in the internal thread 22 of the locking element 14, it advances towards the distal direction, i. e. towards the head of the nail 1. At the same time, this screwing action presses the screw 19 between the locking element 14 and the first transverse hole 9.

By completing the screwing, the plug 15 takes its definitive position with the first stage 8 inserted to close the mouth of the head 4 of the nail 1.

In this way, the screw 19 remains blocked thanks to the interaction between the locking element 14 and the plug 15.

Advantageously, as already shown in FIG. 1, the device 1 also comprises a compression mechanism 30 through an elastic element.

Figure 7B:
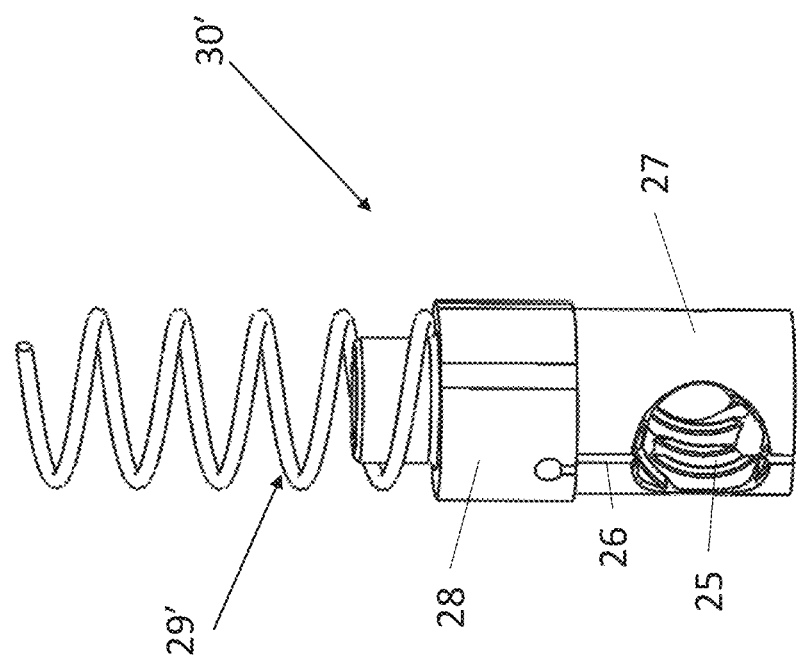
FIGS. 7A and 7B show respective perspective and schematic views of two example of embodiment of a compression mechanism incorporated in the device for arthrodesis according to the invention.
Figure 7A:
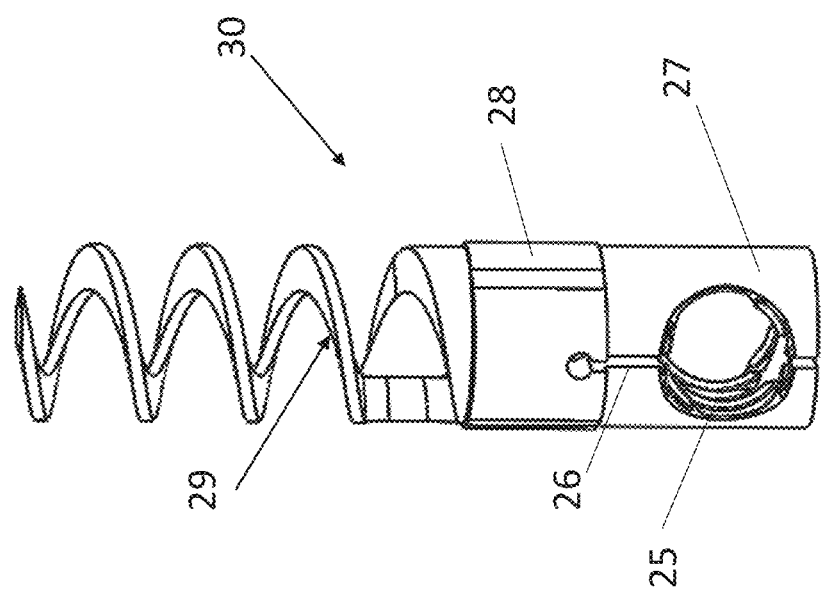

As shown in FIG. 7A, a first embodiment of such a compression mechanism 30 provides a special component formed by a substantially cylindrical base portion 27 in which a transverse hole 25 is obtained.

The transverse hole 25 can be internally threaded, as shown in figure, or without any thread.

In the base portion 27, a longitudinal groove 26 is made which would cut the cylindrical base portion along generatrixes opposed to each other if it were not for the fact that there is an upper annular element 28, with greater diameter, which is like a junction between the base portion 27 and a longitudinally extended helical spring 29.

In a first embodiment, the spring 29 can be integral with the elements 28 and 27 through a helical material removal starting, for example, from a hollow cylinder.

Alternatively, and it is the other embodiment showed in FIG. 7B, an analogous compression mechanism 30' always comprises the base portion 27 and the junction annular element 28 on which a structurally independent spring 29' is fitted.

In both the embodiments, the groove 26 is a cut which interrupts the continuity of the hole 25.

The cut 26 has the purpose to allow a lateral elastic deformation of the hole 25 such that a screw and a pin inserted inside it are stabilized in order to avoid unwanted movements.

The junction annular element 28 has a shape provided to be coupled inside the cavity 6 of the nail 1 such that the translation of the compression mechanism 30 or 30' is allowed, but not the relative rotation between such mechanism and the nail 1.

FIG. 8 shows a prospective and schematic view of the compression mechanism of FIG. 7A inserted inside the nail 1 for arthrodesis according to the invention.

The mechanism 30 is inserted such that the hole 25 is accessible from the slotted transverse second hole 10.

The mechanism 30 is held in position by a threaded dowel 35 which is screwed inside the nail 1 in the thread 12 of the cavity 6 until supporting the mechanism 30 with the hole 25 at the slot 10.

Advantageously, the device 1 is assembled, the compression mechanism 30 leans onto the dowel 35 and is held in position by the elastic force exerted by the spring 29 which is in turn held between the dowel 35 and an internal surface of the nail 1, for example the junction segment 38 between the two communicating cavities 6 and 7 in the distal portion 2.

This expedient allows the alignment between the hole 25 in the component compression mechanism 30 and the lower part of the slot 10 to be guaranteed during the operation. Since the surgical operation of internal fastening requires the use of tools and targeting procedures in order to ensure that the holes are centred from the outside, it is appropriate that the device according to the invention remains stable during the operating stages.

Figure 9:
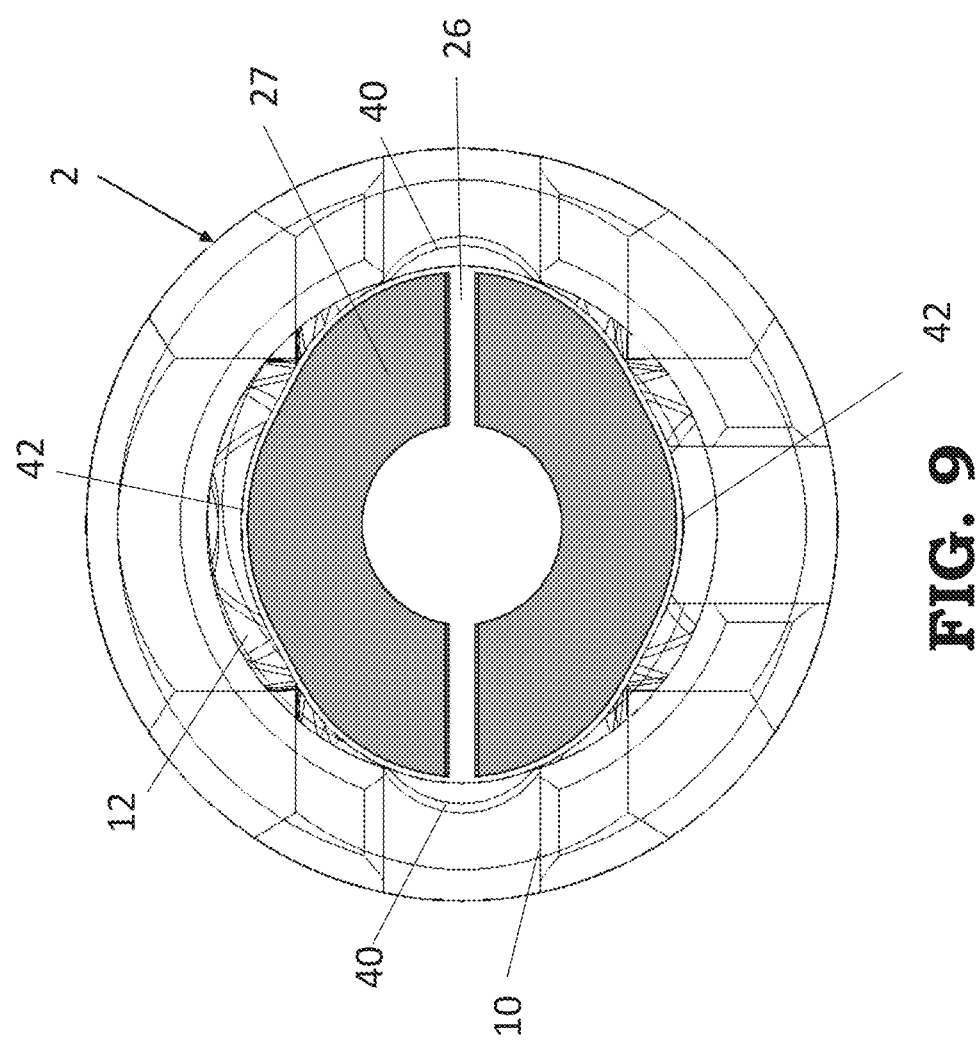
FIG. 9 shows a cross-sectional view of the device of FIG. 8 taken according to the line X-X.

FIG. 9 shows a cross-sectional view of the device of FIG. 8, taken according to the section line X-X.

In the figure, the base portion 27 of the compression mechanism 30 and the respective groove 26 can be seen in section.

Figure 10:
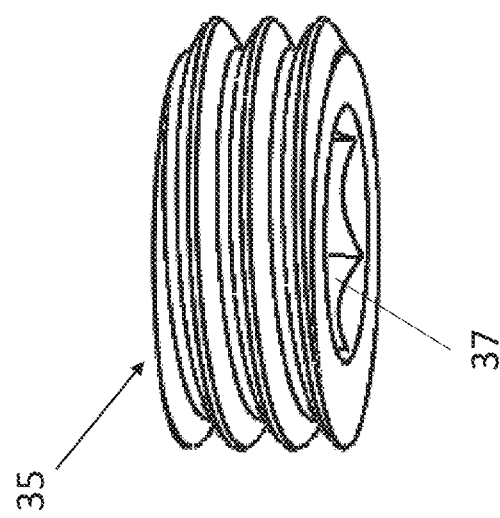
FIG. 10 shows a prospective view of a component of the device according to the invention.

FIG. 10 shows a prospective view of the interposition dowel 35 between the compression mechanism 30 and the underlying screw 19 for fastening to the calcaneus CA.

The dowel 35 has an Allen seat 37 for inserting a manoeuvre wrench (not shown) which allows the surgeon to position the dowel in a screwed manner inside the cavity 6.

Acting with the manoeuvre wrench on the threaded dowel 35, the positioning of the transverse hole 25 of the base portion 27 with respect to the slot 10 can be moved.

Figure 11B:
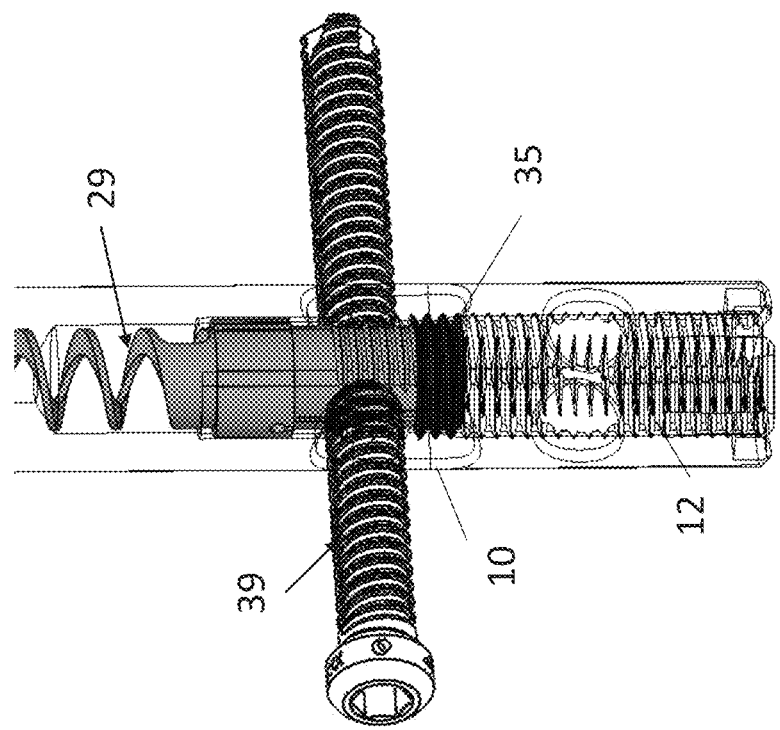
FIGS. 11A and 11B show respective prospective and schematic views of the distal portion of the device according to the invention in two different operating conditions.
Figure 11A:
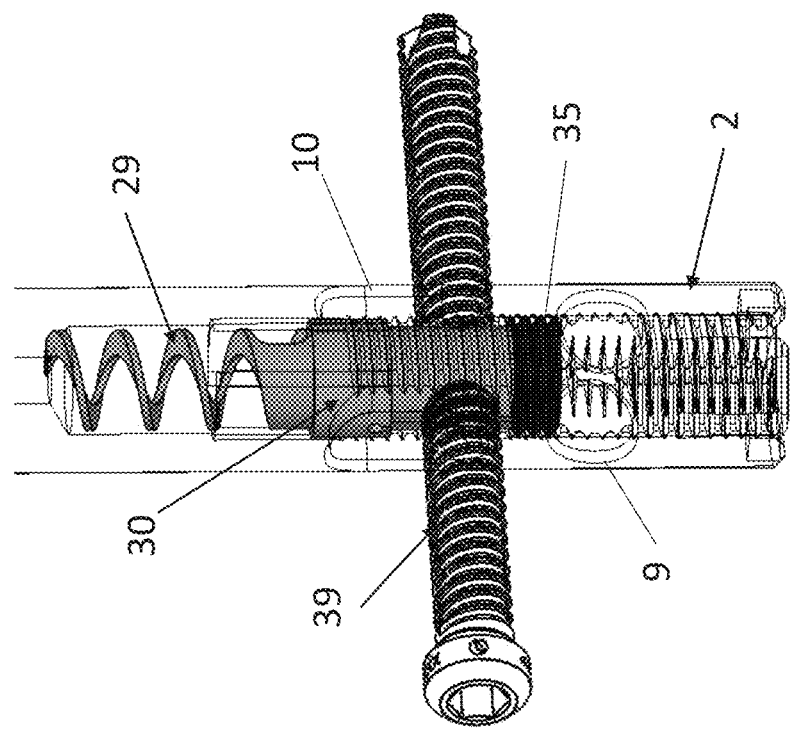

FIG. 11A shows a prospective and schematic view of the compression mechanism 30 inserted inside the distal portion 2 of the nail 1 and lowerly held by the dowel 35 at the lower end of the slot 10.

In this way it is possible to transversally insert a fastening screw 39 which passes through the slot 10 and the transverse hole 25 of the base portion 27 of the mechanism 30.

In FIG. 11B, the same prospective and schematic view is shown in which the dowel 35 was screwed by the operating surgeon deeper into the cavity 6.

This entailed a more proximal support of the mechanism 30 with respect to the constriction 38 inside the distal portion 2 with respective compression of the spring 29.

The image shows how the fastening screw 39 has been brought near the opposite end to the slot 10 by compressing the spring 29 and also compacting the bones which are meant to be fused and in which the screw 39 is screwed.

Basically, the movement of the screw 39 with respect to the slot 10 determines the entity of the compression allowed by the spring 39.

Figure 12:
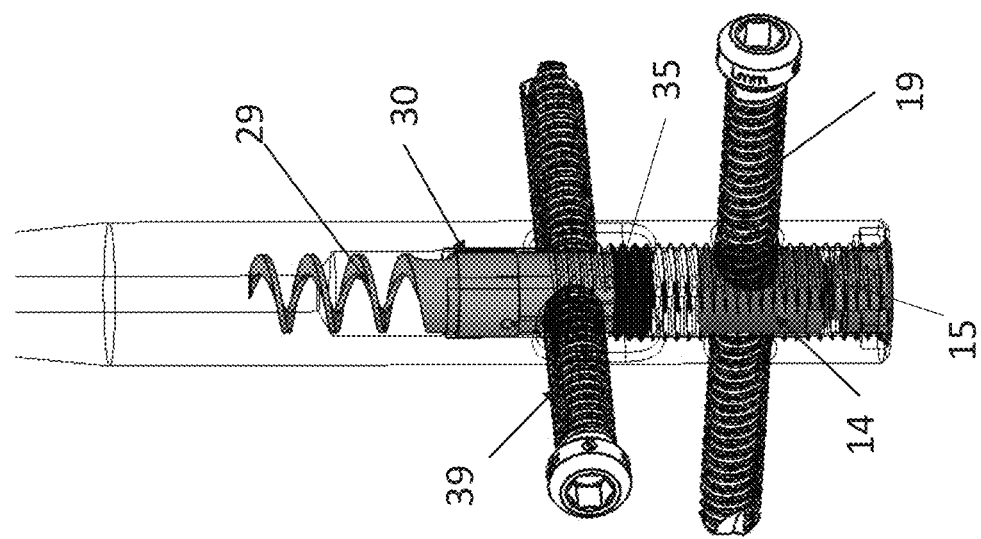
FIG. 12 shows a prospective and schematic view of the improved device for arthrodesis according to the present invention equipped with the component parts illustrated in the previous figures.

In the following FIGS. 12 and 13, it is possible to observe the nail with all its components and the screws 19 and 39 and, successively, the same virtually implanted in a foot-ankle model.

An alternative embodiment of the compression mechanism, which will be indicated with the number 30", is now described with reference to FIGS. 14 15A, 15B, 16A and 16B.

In relation to the previous embodiment of FIGS. 7A and 7B, a first component formed by a sliding body 47 with structure similar to the base portion 27 of the previous embodiment, is shown. This body 47 is partially elastic or has an elastic component, even if the respective deformations take place in the elasticity field of the material.

The sliding body 47 has an almost cylindrical distal portion 48 with a transverse hole 45 provided to accommodate the screw 39 of the fastening means and a more proximal cap portion 49 having a greater diameter, substantially corresponding to the internal diameter of the cavity 6.

A second component of the compression mechanism 30" is a dowel 55 having a cylindrical short axial protrusion 57 coaxially projecting from a side. This protrusion 57 has a free annular end having an edge 58 with tooth profile in order to engage with a snap-fit in a corresponding circular seat 43 obtained in the distal part 46 of the previous component 47, as will be described in detail below.

The dowel 55 is externally threaded and has an Allen end as the dowel 35 of FIG. 10.

Figure 15A:
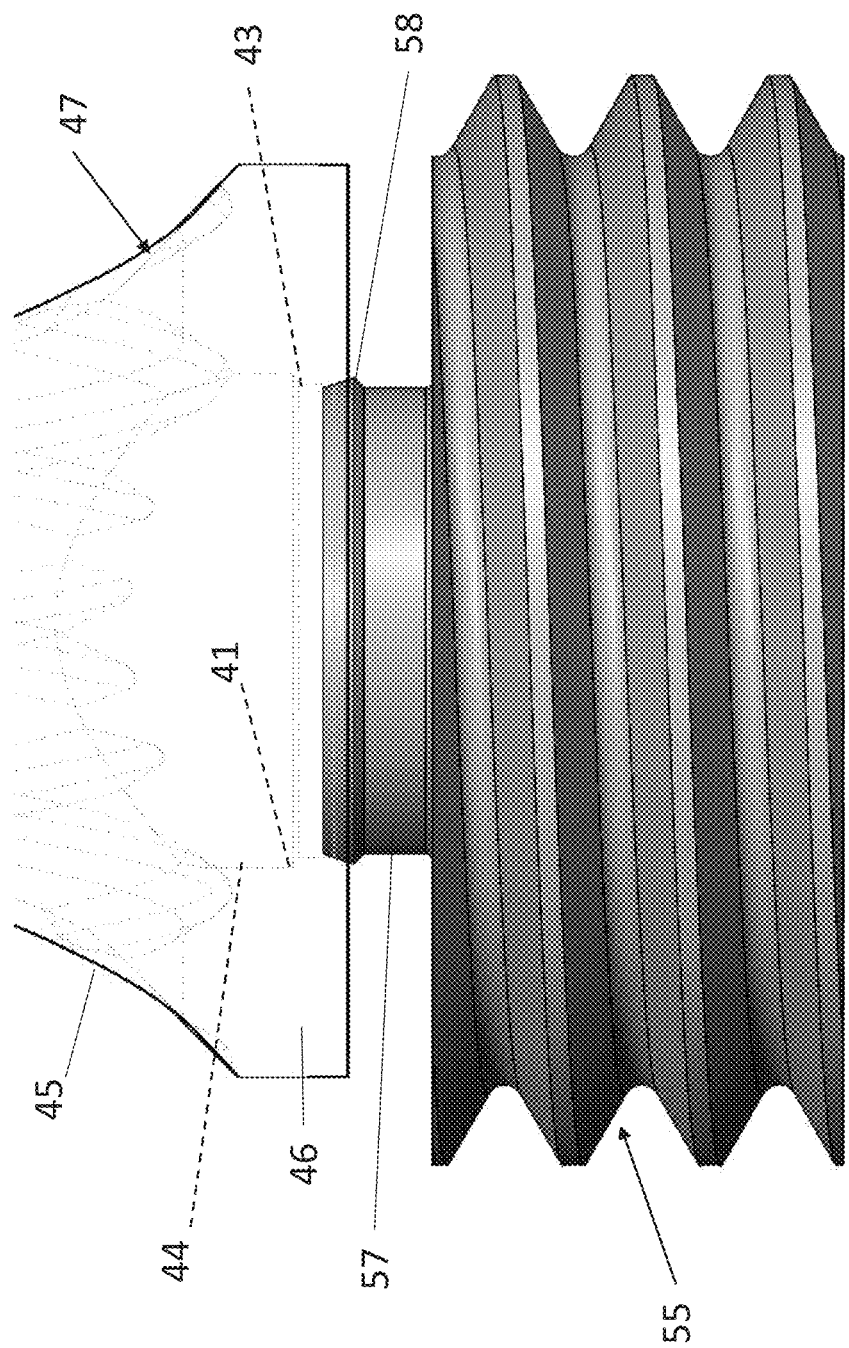
FIGS. 15A and 15B show respective enlarged-scale lateral views of an engagement between the components of the compression mechanism of FIG. 14 in two different operating conditions.

FIG. 15A shows a first proximity view in which the two components 47 and 55 of the compression mechanism 30" are about to be rotably coupled with each other.

In other words, two components 47 and 55 are interconnected in a stable way but are able to rotate in a relative way.

This is made possible by their respective structure since the sliding body 47 is cannulated and has an internal cylindrical cavity 44, which is coaxial to its longitudinal axis and, at the distal end 46, has a diameter reduction which defines the circular seat 43 with limited height and creates an internal step 41 or stair with the cavity 44 with greater diameter.

As previously said, the dowel 55 has an axial protrusion 57 which faces in the proximal direction with the edge 58 with tooth profile which is facing the circular seat 43 of the distal part 46 of the sliding body 47.

Figure 15B:
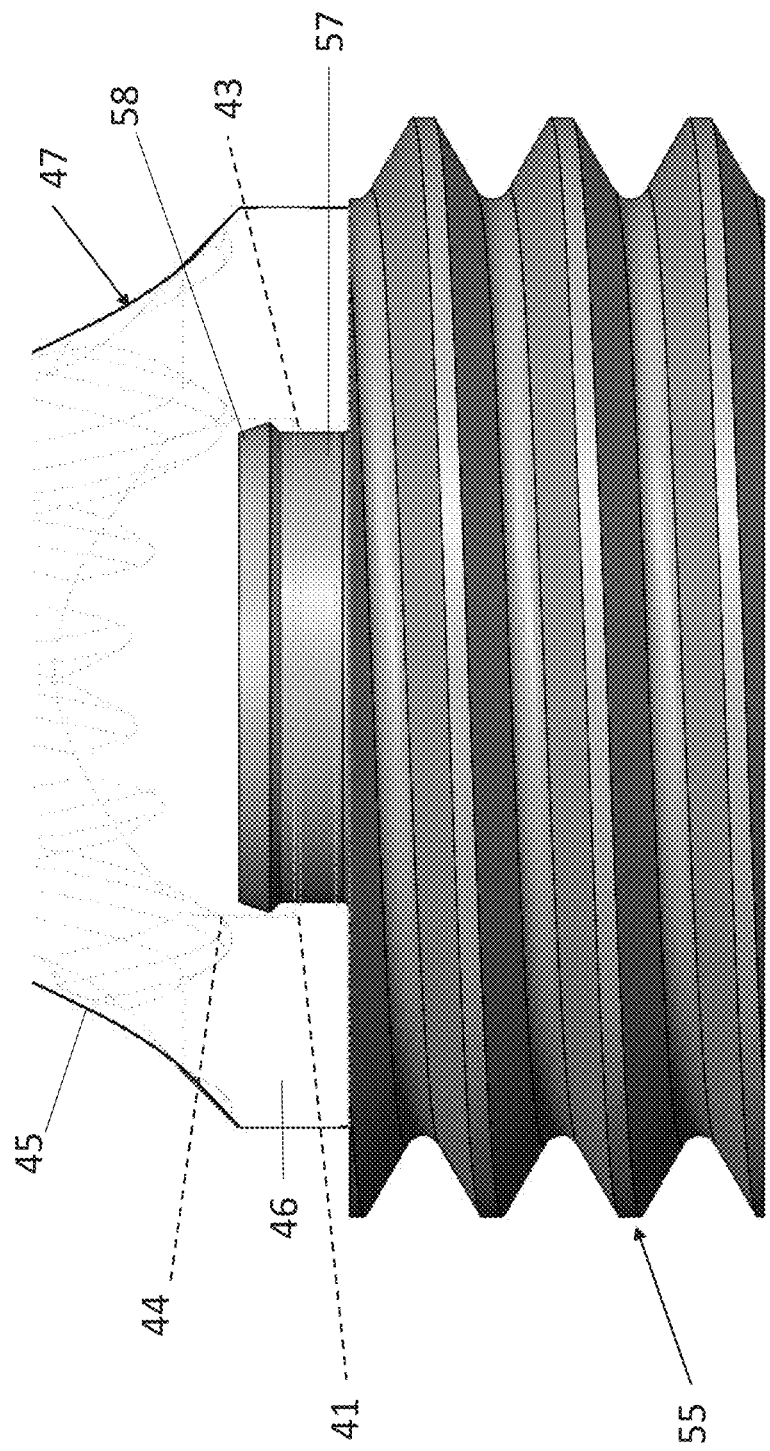
Figure 18:
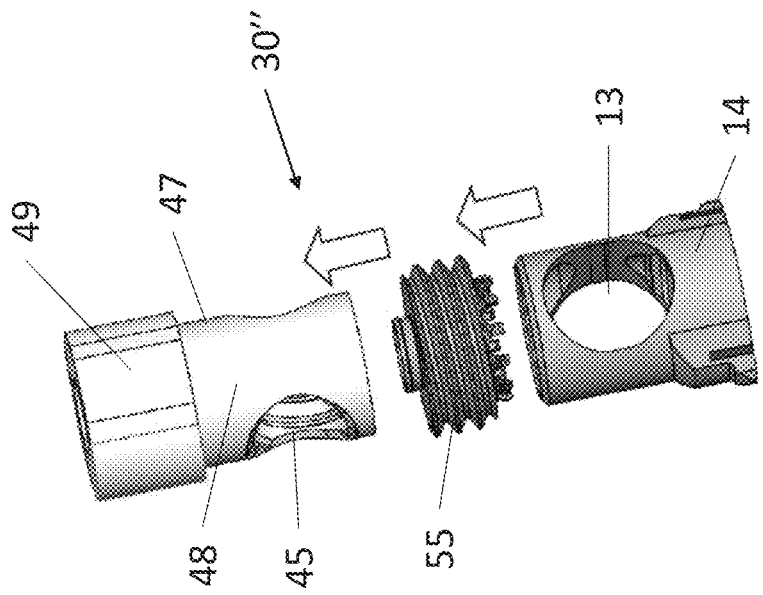
FIG. 18 shows a prospective view of the compression mechanism of FIG. 17 in a detached configuration.
Figure 17:
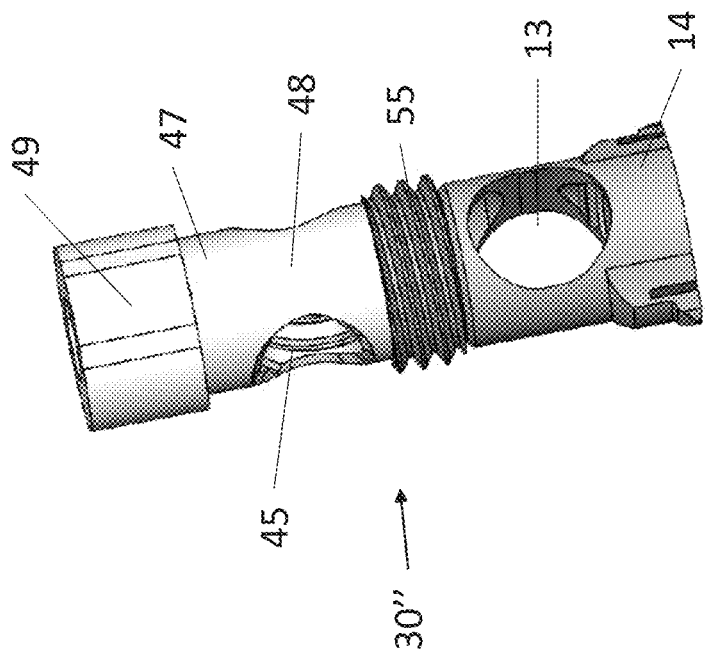
FIG. 17 shows a prospective view of a further example of embodiment of a compression mechanism incorporated in the device for arthrodesis according to the invention.
Figure 20:
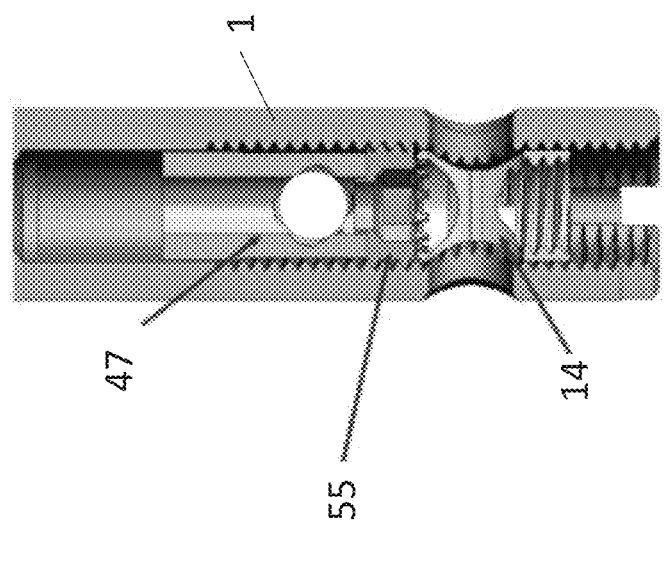
FIG. 20 shows a lateral cross-section of the head of the nail according to the invention equipped with the compression mechanism illustrated in FIGS. 17-19.
Figure 19:
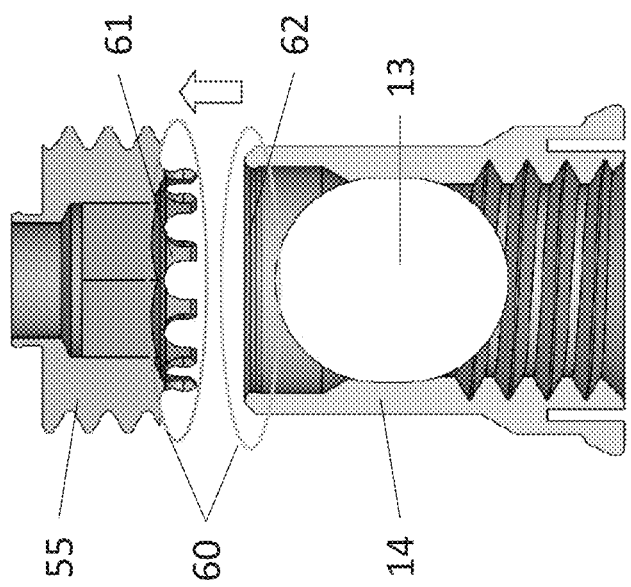
FIG. 19 shows a lateral cross-section of two detached components of the compression mechanism of FIG. 17.

FIG. 15B shows the same components of FIG. 15A in a mutual coupling configuration in which it is evident the clearance which allows the relative rotation between the two components 47 and 55.

The edge 58 with tooth profile passed the circular seat 43 in proximal direction and is accommodated in the distal part of the cylindrical cavity 44 but it can no longer return in distal direction because of the step 41.

The result is that the dowel 55 is free of rotating with respect to the sliding body 47 but the two components are stably coupled with each other.

It should be mentioned that, in an operating configuration, the sliding body 47 is crossed by the fastening screw 39 which is implanted by screwing in the respective portion of the calcaneus CA.

The two components 47 and 55 act as one and can be inserted in the previously described same nail 1 by rotating the threaded dowel 55 with a manoeuvre wrench and causing it to advance in proximal direction in the thread 12. In this way, a compression not only of the sliding body 47 but also of the transverse screw 39 crossing the hole 45 and the slot 10, when the device is implanted in the foot of the patient, takes place.

Accordingly, a corresponding compression is obtained in mutual approaching of the bones, in which the screws 19 and 39 are implanted.

FIGS. 16A and 16B show respective prospective and schematic views of the improved device for arthrodesis according to the example of embodiment of the compression mechanism in the two configurations of first implantation and maximum compression.

An alternative embodiment of the compression mechanism, which will be indicated with the number 30''', is now described with reference to FIGS. 17, 18, 19 and 20.

With reference to the embodiment of FIGS. 14, 15A, 15B, 16A and 16B, the compression mechanism comprises a sliding body like the previously described sliding body 47 and a dowel like the previously described dowel 55. These components and their parts or features are shown in the figures with the same reference numbers employed for the previous embodiment, and the previous description applies to them unless otherwise stated in the following.

As discussed in the previous embodiment, two components 47 and 55 are interconnected in a stable way but they are able to rotate in a relative way, and the dowel can be engaged by a wrench in order to regulate the position of the fastening screw 39 accommodated by the sliding body.

Further, the compression mechanism 30" comprises a sleeve locking element 14 like the one previously described and shown in FIGS. 5 and 6. Again, this component and its parts or features is shown in FIGS. 17-20 with the same reference numbers employed for the previous embodiments, and the previous description applies unless otherwise stated in the following.

However, in the present embodiment of the compression mechanism the dowel 55 and the sleeve 11 of the sleeve locking element 14 are provided with releasable latching means 60, which temporarily interconnect the two components in an initial setup of the device.

The releasable latching means 60 comprise, on one side, a plurality of elastic teeth 61 and, on the other side, a seat 62 where the elastic teeth 61 can engage with snap-fit. In the represented embodiment, the elastic teeth 61 are engaged along the distal annular periphery of the dowel 55, whereas the seat 62 is an annular groove provided on an internal surface of the proximal end of the sleeve 11. However, the elastic teeth 61 could be provided on the proximal annular periphery of the sleeve 11 and the groove could be made on the dowel 55.

Thanks to the releasable latching means 60, the sliding body 47, the dowel 55 and the sleeve 11 form a single assembly, and they can be manipulated together when the device is implanted. The releasable latching means do not hinder relative rotation of the dowel 55 and sleeve 11, so that the dowel 55 can be rotated by means of a wrench even when it is coupled to the sleeve 11. However, when the dowel 55 is rotated and translated along the nail 1 together with the sliding body 47, allowing compression to take place, the releasable latching means 60 disengage, so that the dowel 55 and sliding body 47 are no longer constrained to the sleeve 11.

Figure 21A:
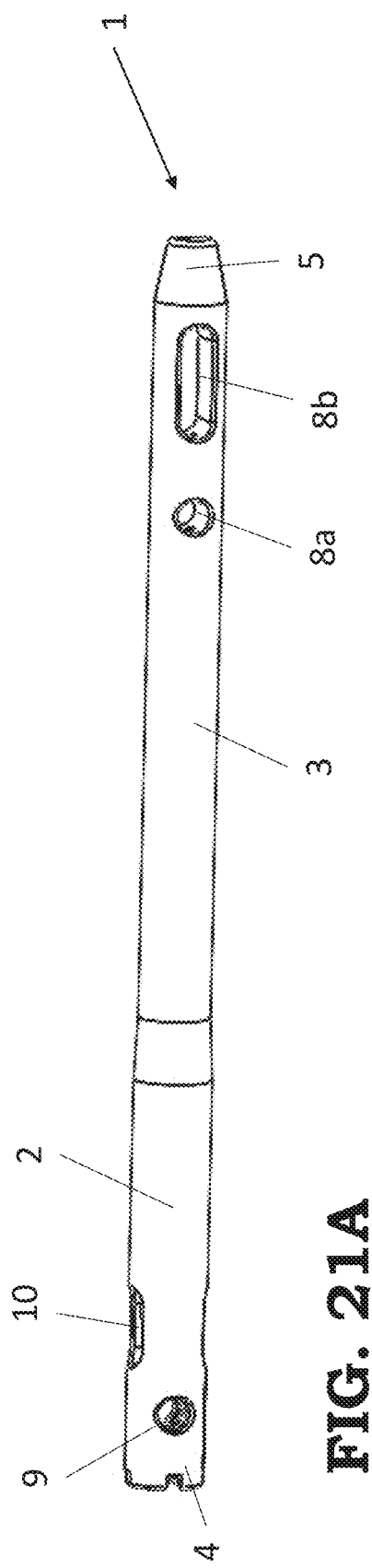
FIG. 21A shows a prospective view of a first embodiment of a nail according to the invention.
Figure 21B:
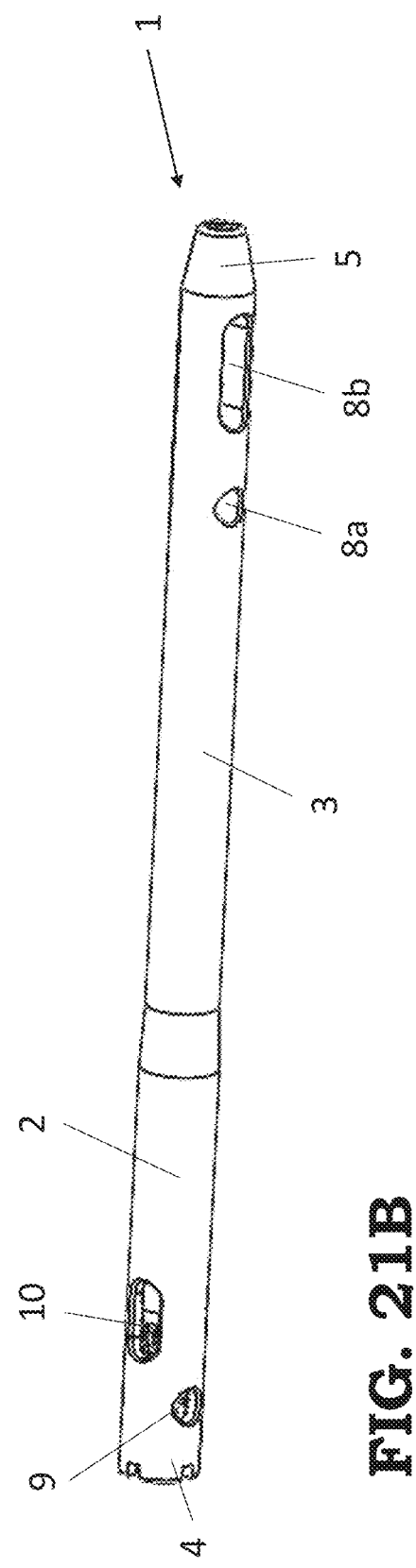
FIG. 21B shows a prospective view, under a different angle, of the nail of FIG. 21A.

FIGS. 21A and 21B show a complete view of the first embodiment of the nail 1, in which the tip 5 is visible. The tip 5 customarily has holes 8a, 8b for the insertion of bone screw traversing the patient's tibia: in the present embodiment, a distal circular hole 8a and a proximal slotted hole 8b are provided.

FIGS. 22A and 22B show a complete view of a second embodiment of the nail 1', in which the tip 5 is visible. In this embodiment, the proximal portion of the shaft features, in addition to the holes 8a, 8b at the tip which are the same as in the first embodiment, an intermediate circular hole 8c and an intermediate slotted hole 8b.

Advantageously, the device according to the present invention is implanted by a surgical method which provides that the distal portion 2 is oriented towards the rear part of the ankle of the patient, with the first hole 9 arranged and orientated to receive and guide the first fastening means 19 along a first fastening direction which extends through the calcaneus CA.

The nail 1 is positioned in the ankle joint of the patient. Advantageously, this first installation step can be preceded by a preparatory step during which a housing crossing calcaneus CA, talus TL (if present) and tibia TB is created, using any known means (for example a drill), in order to subsequently receive the nail 1. Preferably, this housing is made so as to allow the implantation of said nail 1 in a retrograded plantar way.

Figure 13:
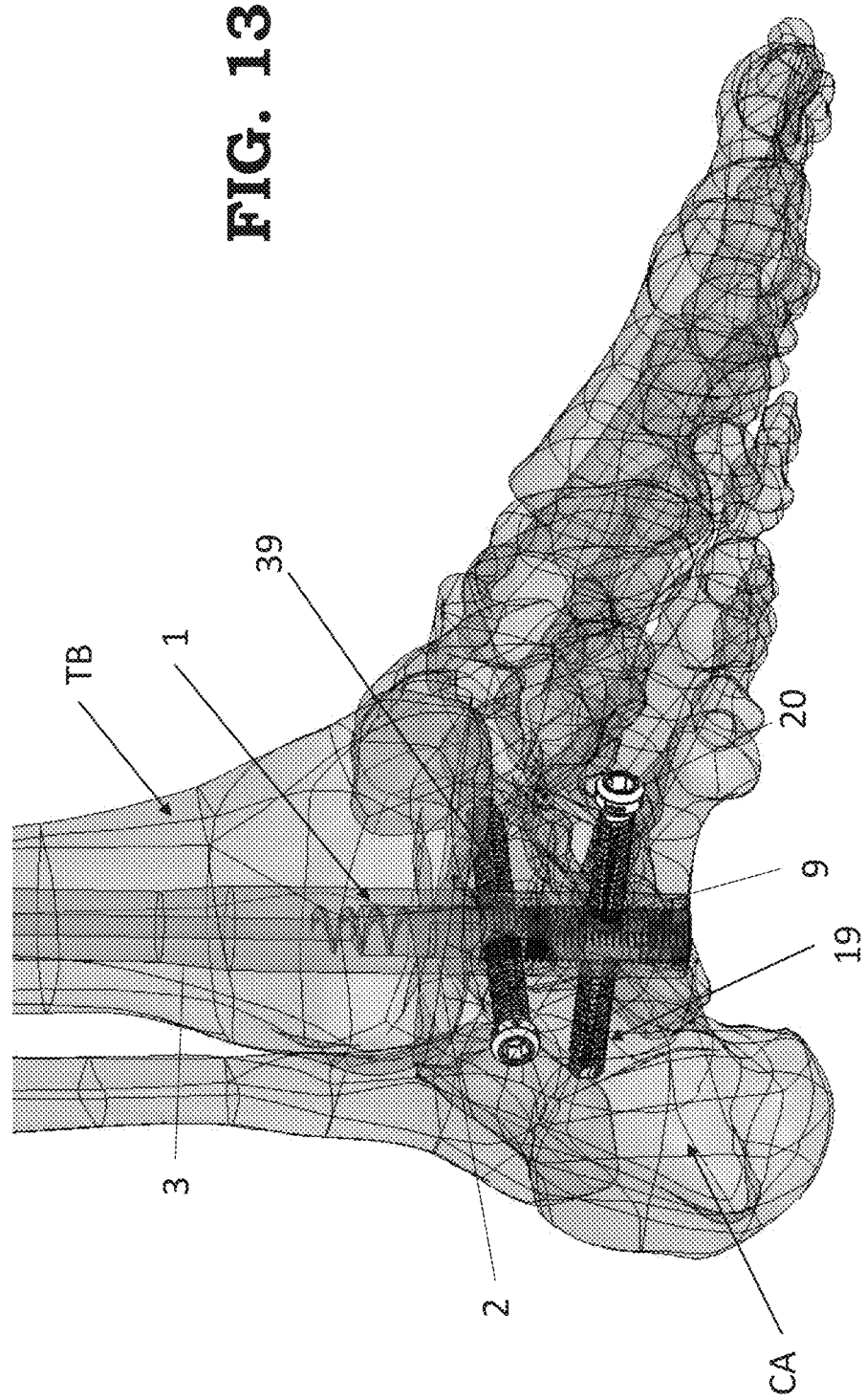
FIG. 13 illustrates a prospective schematic and partial view of the improved device for arthrodesis according to the present invention and shown implanted in a human foot, however, according to a different angle with respect to FIG. 1.
Figure 14:
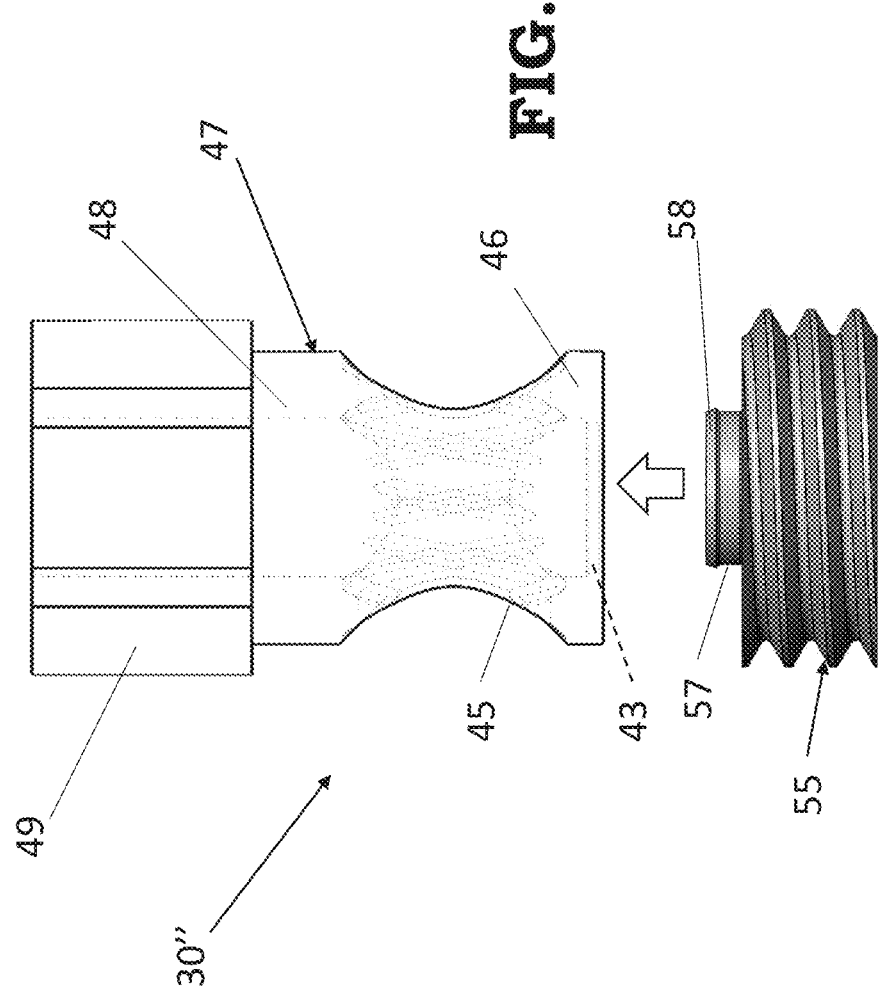
FIG. 14 shows a vertical elevation schematic view of a further example of embodiment of a compression mechanism incorporated in the device for arthrodesis according to the invention.

Preferably, the positioning of the nail 1 takes place such that the screwing direction of the first screw fastening means 19 is oriented in a mediolateral direction, as can be seen in FIG. 13, substantially towards the rear part of the ankle of the patient.

Preferably, the second screw fastening means 39 are extended in a direction perpendicular to the first screw fastening means 19 so as to be always able to implant themselves in the calcaneus CA, as shown in FIG. 1 or in FIG. 13. It is thanks to the compression mechanism 30, 30' or 30" of the device 1 according to the invention that the ankle bones are compressed in order to also compress the talus (if present) against the tibia and allow a fusion between the bones to take place.

It will be actually practically noted that the terms "first", "second", "third", etc. used in the present description preferably have no ordinal or cardinal connotation, i.e. they do not imply here any notion of order, quantity or qualification of the elements or components to which these terms are attached. Their purpose in this case is only to ease the understanding of the invention, making it possible to differentiate some technical features from each other which the arthrodesis device according to the invention can have, as well as the various stages which can advantageously include the surgical method which advantageously aimed to the implementation of said arthrodesis device.

Furthermore, the terms "rear", "front", "medial" and "lateral" are preferably used in the present invention in order to qualify the elements or the features related to their respective orientation with respect to the body of the patient, in the normal use of the arthrodesis device according to the invention, and in particular of the nail 1 of the latter. Therefore, the term "medial" is preferably used in order to define an element or component of the arthrodesis device which is provided to be positioned and oriented on the side closest to the mid-sagittal plane (or mid axis) of the body of the patient, in other words the side facing inside the ankle and the leg of the patient. Conversely, the term "lateral" is used in relation to the side furthest away from the mid-sagittal axis. Following the same logic, the terms "rear" and "front" respectively preferably refer to a positioning towards the rear part, respectively towards the front part, with respect to the front plane of the patient.

The invention finds its application in designing and manufacturing devices provided to be used for carrying out an arthrodesis and, more specifically, in designing and manufacturing devices provided to be used for carrying out an arthrodesis of the joint of an ankle, especially in the context of orthopaedic treatment.

The invention claimed is:

1. Improved orthopaedic device for ankle arthrodesis, in particular for the arthrodesis or fusion of a joint, for example an ankle joint, of the type comprising:
   a nail having a distal head and a proximal tip ends opposed to each other;
   at least a distal first portion of the nail having an axis of symmetry;
   at least a proximal second portion of the nail;

distal holes for the insertion of bone screws traversing a tibia of a patient made in the proximal second portion;

a single circular first transverse hole made in the distal first portion near the distal head of the nail and with an axis extending perpendicularly to the axis of symmetry; and a slotted second transverse hole still made in the distal first portion of the nail and extended perpendicular to both the axis of symmetry, and to the axis of the single circular first transverse hole;

the slotted second transverse hole being made at a greater distance with respect to the distal head of the nail than the distance from the single circular first transverse hole;

wherein the distal holes are arranged to accommodate bone screws oriented along a mediolateral direction of the tibia, the single circular first transverse hole is arranged to accommodate a bone screw oriented along a mediolateral direction in a calcaneus of the patient and the slotted second transverse hole is arranged to accommodate a fastening screw oriented along a posteroanterior direction in the calcaneus.

2. The orthopaedic device according to claim 1, wherein the distal first portion of the nail has an internal cavity extended starting from the distal head along the axis of symmetry and internally comprising a thread extended up to at least the slotted second transverse hole.

3. The orthopaedic device according to claim 2, wherein the thread is extended up to at least 80% of the slotted second transverse hole.

4. The orthopaedic device according to claim 2, comprising a compression mechanism with an elastic element inserted in the distal first portion of the nail between a support dowel screwed into the thread of the internal cavity and a constriction of the distal first portion, a transverse hole being provided in a base portion of the compression mechanism to be accessible through the slotted second transverse hole.

5. The orthopaedic device according to claim 4, wherein the base portion of the compression mechanism partially comprises a longitudinal groove.

6. The orthopaedic device according to claim 5, wherein the elastic element is a helical spring integral with the base portion or associated in a structurally independent manner to the base portion.

7. The orthopaedic device according to claim 2, comprising a compression mechanism with a sliding body inserted in the distal first portion of the nail between a support dowel screwed into the thread of the internal cavity and a constriction of the distal first portion, a transverse hole being provided in an elastic body of the compression mechanism to be accessible through the slotted second transverse hole, the support dowel and the sliding body being rotably coupled with each other.

8. The orthopaedic device according to claim 7, wherein the sliding body is internally cannulated and it has an end portion with a diameter change to form a step while the support dowel has an axial protrusion with an end annular edge with tooth profile to be snap-coupled to the end portion with rotatable coupling abutting said step.

9. The orthopaedic device according to claim 7, wherein the support dowel is temporarily coupled sleeve locking element inserted in the distal first portion of the nail and provided with a transverse hole accessible through the single circular first transverse hole.

10. The orthopaedic device according to claim 1, comprising fastening means inserted in the single circular first transverse hole passing through a locking element inserted inside the distal first portion of the nail.

11. The orthopaedic device according to claim 1, comprising a closing plug for the distal head of the nail structured with a first stage fastened to a free end of the distal head and an internal second stage in engagement with a sleeve locking element inserted in the distal first portion of the nail and provided with a transverse hole accessible through the single circular first transverse hole.

12. The orthopaedic device according to claim 11, wherein the sleeve locking element is made of a biocompatible and implantable material which works in the elastic field.

13. The orthopaedic device according to claim 11, wherein the sleeve locking element is internally threaded up to the transverse hole to be engaged by an external thread of the internal second stage.

14. The orthopaedic device according to claim 11, wherein the sleeve locking element comprises two guiding and stabilizing appendices opposed to each other provided for a frictional engagement in corresponding lateral concavities of an internal cavity of the distal first portion of the nail and extended starting from the distal head along the axis of symmetry up to passing the single circular first transverse hole.

15. The orthopaedic device according to claim 1, wherein, the single circular first transverse hole and the slotted second transverse hole are the only transverse holes provided in the distal first portion of the nail, no transverse hole being provided at a talus of the patient.

16. Improved orthopaedic device for ankle arthrodesis, in particular for the arthrodesis or fusion of a joint, for example an ankle joint, of the type comprising:

a nail having a distal head and a proximal tip ends opposed to each other;

at least a distal first portion of the nail having an axis of symmetry;

at least a proximal second portion of the nail;

a single circular first transverse hole made in the distal first portion near the distal head of the nail and with an axis extending perpendicularly to the axis of symmetry;

a slotted second transverse hole still made in the distal first portion of the nail and extended perpendicular to both the axis of symmetry, and to the axis of the single circular first transverse hole;

the slotted second transverse hole being made at a greater distance with respect to the distal head of the nail than the distance from the single circular first transverse hole;

wherein the single circular first transverse hole is arranged to accommodate a bone screw oriented along a mediolateral direction in a calcaneus of a patient and the slotted second transverse hole is arranged to accommodate a fastening screw oriented along a posteroanterior direction in the calcaneus; and a closing plug for the distal head of the nail structured with a first stage fastened to a free end of the distal head and an internal second stage in engagement with a sleeve locking element inserted in the distal first portion of the nail and provided with a transverse hole accessible through the single circular first transverse hole;

wherein the sleeve locking element is internally threaded up to the transverse hole to be engaged by an external thread of the internal second stage.

17. The orthopaedic device according to claim 16, wherein the sleeve locking element comprises two guiding and stabilizing appendices opposed to each other provided for a frictional engagement in corresponding lateral concavities of an internal cavity of the distal first portion of the nail and extended starting from the distal head along the axis of symmetry up to passing the single circular first transverse hole.

18. Improved orthopaedic device for ankle arthrodesis, in particular for the arthrodesis or fusion of a joint, for example an ankle joint, of the type comprising:
- a nail having a distal head and a proximal tip ends opposed to each other;
- at least a distal first portion of the nail having an axis of symmetry;
- at least a proximal second portion of the nail;
- a single circular first transverse hole made in the distal first portion near the distal head of the nail and with an axis extending perpendicularly to the axis of symmetry;
- a slotted second transverse hole still made in the distal first portion of the nail and extended perpendicular to both the axis of symmetry, and to the axis of the single circular first transverse hole;
- the slotted second transverse hole being made at a greater distance with respect to the distal head of the nail than the distance from the single circular first transverse hole;

wherein the single circular first transverse hole is arranged to accommodate a bone screw oriented along a mediolateral direction in a calcaneus of a patient and the slotted second transverse hole is arranged to accommodate a fastening screw oriented along a posteroanterior direction in the calcaneus;

wherein the distal first portion of the nail has an internal cavity extended starting from the distal head along the axis of symmetry and internally comprising a thread extended up to at least the slotted second transverse hole; and
- a compression mechanism with an elastic element inserted in the distal first portion of the nail between a support dowel screwed into the thread of the internal cavity and a constriction of the distal first portion, a transverse hole being provided in a base portion of the compression mechanism to be accessible through the slotted second transverse hole.

19. The orthopaedic device according to claim 18, wherein the base portion of the compression mechanism partially comprises a longitudinal groove.

20. The orthopaedic device according to claim 19, wherein the elastic element is a helical spring integral with the base portion or associated in a structurally independent manner to the base portion.

* * * * *